United States Patent [19]

Tenczar

[11] 4,019,512
[45] Apr. 26, 1977

[54] ADHESIVELY ACTIVATED STERILE CONNECTOR

[76] Inventor: Francis J. Tenczar, P.O. Box 42919, Evergreen Park, Ill. 60642

[22] Filed: Dec. 4, 1975

[21] Appl. No.: 637,750

[52] U.S. Cl. .................... 128/214 R; 128/214.2; 285/3

[51] Int. Cl.$^2$ .............. A61M 5/14; F16L 37/24

[58] Field of Search ........ 128/214 R, 214.2, 218 P, 128/218 PA, 221, 349 R, 272; 285/3, 4, DIG. 16

[56] References Cited

UNITED STATES PATENTS

| 2,933,333 | 4/1960 | Bredtschneider et al. ........... 285/3 |
|---|---|---|
| 2,958,545 | 11/1960 | Stelzer ................... 285/3 |
| 3,037,796 | 6/1962 | Robb ..................... 285/3 |
| 3,131,952 | 5/1964 | D'Esopo ................. 285/3 |
| 3,148,894 | 9/1964 | Schwab ................... 285/3 |
| 3,201,148 | 8/1965 | Shurtleff ................. 285/3 |
| 3,202,442 | 8/1965 | Abbey et al. ............. 285/3 |
| 3,246,919 | 4/1966 | Todd .................... 285/3 X |
| 3,285,627 | 11/1966 | Kozulla et al. ........... 285/3 |
| 3,306,563 | 2/1967 | Soto ................... 128/272 X |
| 3,391,951 | 7/1968 | Miller .................. 285/3 |
| 3,399,759 | 9/1968 | Love ................... 128/272 X |
| 3,466,065 | 9/1969 | Acker et al. ............ 285/3 |
| 3,469,581 | 9/1969 | Burke .................. 128/221 |
| 3,491,757 | 1/1970 | Arce ................... 128/221 |
| 3,701,548 | 10/1972 | McGuire ............... 285/DIG. 16 |
| 3,865,411 | 2/1975 | Rowe et al. ............ 285/DIG. 16 |
| 3,900,223 | 8/1975 | Schafer et al. ......... 285/4 |
| 3,902,489 | 9/1975 | Carter ................. 128/214 R |
| 3,909,910 | 10/1975 | Rowe et al. ............ 128/214 R |
| 3,938,520 | 2/1976 | Scislowicz et al. ..... 128/214 R |
| 3,955,833 | 5/1976 | Silbert ................ 285/3 |

FOREIGN PATENTS OR APPLICATIONS 1,300,635 8/1969 Germany ................. 128/214 R Primary Examiner—Edgar S. Burr
Assistant Examiner—Paul J. Hirsch
Attorney, Agent, or Firm—Dominik, Knechtel, Godula & Demeur

[57] ABSTRACT

A sterile connector assembly for moving blood component preparations through a fluid path established by engaged coupling elements within adjoined connectors. The open end of the connectors are closed by barrier membranes covered by protective members with adhesive film between the protective members and the barrier membranes. A pressure cap is mounted on one of the connectors to apply pressure to the adjoining connectors so that the membranes adhere to each other along a sterile surface which is substituted for the non-sterile protective member that is progressively pulled away. A penetrator member associated with one of the coupling elements penetrates the adjoined and adhered membranes so that an associated coupling element can engage the coupling element in the other connector.

16 Claims, 11 Drawing Figures

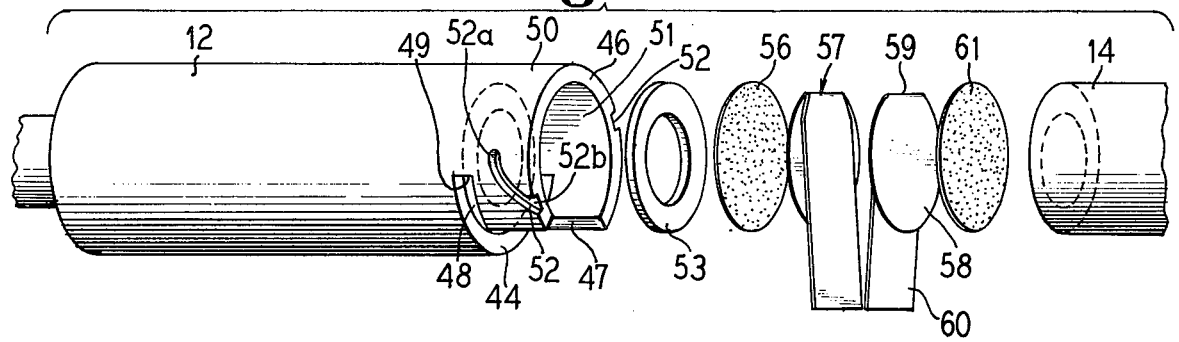
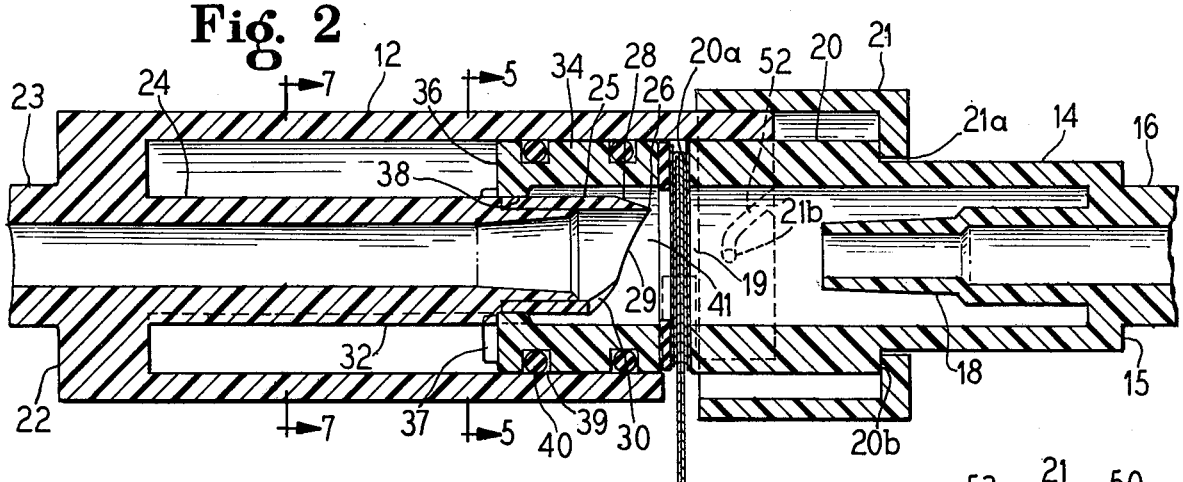
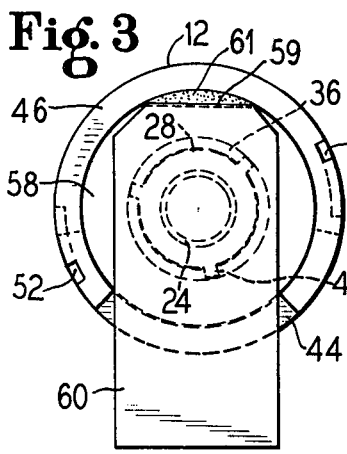
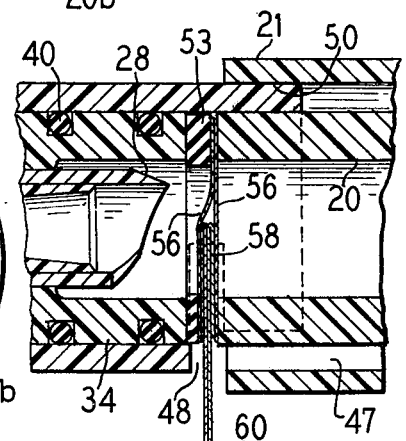
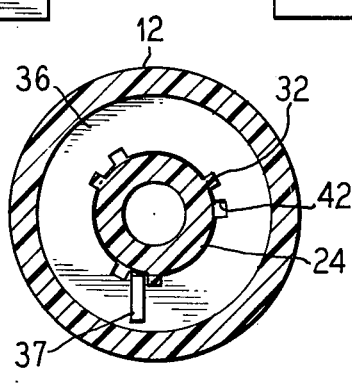

ADHESIVELY ACTIVATED STERILE CONNECTOR

This invention relates to connector assemblies; and particularly relates to connector assemblies in which connector parts are joined in an improved manner which precludes occurrance of environmental contamination. In particular and useful practice, a sterile connector assembly is provided for connecting one fluid source to another, such as blood component preparations.

The art has recognized the desirability of sterile connectors for blood component preparations. See, for example, The DHEW Publication No. (NIH) 76-1004, Frozen Blood Outdating, P. B. Sherer. The applicant herein has disclosed means for attaining such sterile connection in co-pending U.S. patent application Ser. No. 412,553 filed Nov. 5, 1973. In such copending application, a connector assembly has been shown which provides alignment of connector elements, including penetratable barriers held to each other by an adhesive film. A penetrator in one of the connectors then ruptures the penetratable barrier and the internal coupling elements are engaged to each other. Sterility within the connector is retained by adhesively bonding barrier membranes to preclude environmental contamination or by simultaneous penetration fusion and sterilization of plastic membrane barriers using a "hot wire."

It would be desirable to assure a sterile interface area between adjoining penetratable membranes without requiring added steps to assure sterilization.

Sterile connectors are variously joined by coupling one connector to another, a fluid path being provided by such connection. The continuing concern in this art is the hazard of contaminating the connecting interface prior to actual connection. Any such environmental exposure, at least theoretically, creates the possibility of contamination. One promising attempt to solve this problem has been disclosed in U.S. Pat. No. 3,865,411 where each of the couplers have compressible gaskets and a pull tab is adhesively connected to each of the gaskets. The gaskets are placed in face to face relationship and the free end of the folded tabs are jointly pulled away to progressively replace a contaminated surface by a sterile surface. The adhesive functions only to hold the pull tab and not to adhere the gaskets. Avoidance of contamination by environmental exclusion is attained by a clamping means which tightly squeezes the elastomeric gaskets together during removal of the pull tabs and transfer of the fluid.

It is accordingly one important object of the present invention to provide connectors which can be joined together in an improved way to preclude environmental contamination, by utilizing pull tab protective members in a particularly new and improved way to achieve environmental exclusion simultaneously with substituting of a sterile interface for a non-sterile surface.

Another important object of the invention is to provide a sterile connector for blood component preparations in which barrier membranes are protected by protective pull tab members, and such pull tabs are used in an advantageous way to help orientate the connectors relevant to each other and to manipulate elements located within such connectors.

Still yet another important object of the present invention is to provide a sterile connector for blood component preparations with improved means for positively aligning connector components and assuring positioning of coupling elements in accordance with predetermined orientation.

Still yet another important object of the present invention is to provide sterile connectors for blood component preparations in which connector components are entirely self-contained and do not require special means such as sustained pressure for environmental exclusion or additional sterilizing means. It is an aspect of this and other objects that the sterile connector assembly is used simply and conveniently to provide a coupling connection with environmental exclusion provided simultaneously during the coupling operation.

The foregoing objects are attained together with still other objects which will occur to practitioners by the invention which is shown in the following disclosure, which includes drawings wherein:

FIG. 1 is an exploded perspective view of the connector assembly, with portions removed for purposes of clarity;

FIG. 2 is a side elevational view in section of the connector assembly on an enlarged scale;

FIG. 3 is an end elevational view of the barrier end of the female connector shown in the assembly of FIG. 2;

FIG. 4 is an end elevational view of the barrier end of the male connector shown in the assembly of FIG. 2;

FIG. 5 is a sectional view taken along line 5—5 in FIG. 2;

FIG. 6 is a side elevational sectional view similar to that of FIG. 2, but with portions removed and depicting the substitution of the sterile surface for the non-sterile surfaces;

Figure 7:
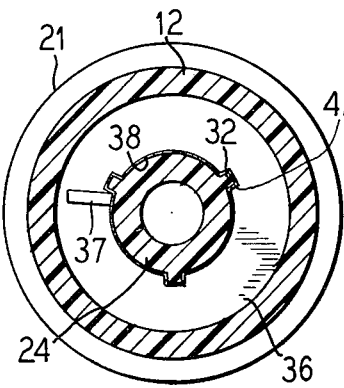
FIG. 7 is a sectional view taken along line 7—7 in FIG. 2, but showing seal member in rotated position to align keys on the penetrator and the seal member.

The invention provides two connector components in which the open end of each connector is closed by a penetratable barrier. A film of adhesive is on each barrier and a removable protective member covers the film and barrier. Each of the connector components houses a coupling element, one of the coupling elements being associated with a penetrator element. The respective penetratable barriers are aligned in face to face relationship, placed under pressure and the protective members are removed. Progressive portions of adhesive film are deposited on the barrier membranes while sterile protecting pull tabs are removed and the sterile surface is simultaneously substituted for the contaminated surface. The adjoined and adhered barriers are then ruptured by the penetrator-coupling element and the other coupling element is engaged.

The penetrator element and the barrier assembly are relatively movable, as with a stationary penetrator element and a movable barrier assembly; or with a stationary barrier assembly and a movable penetrator element. Preferably, the connector components are positively aligned by providing a curved shroud extending from one of the connector component elements, the other connector component fitting within said shroud. The inner end of the shroud is provided with a slot for admitting and aligning the pull handles. The shroud also has an undercut for withdrawing the protective covers which have dimensions similar to the barrier membranes. Aligning such pull tabs orientates the two connector components, and such aligned tabs can be pulled away to remove the protective members through the undercut zone.

The connector component housing the penetrating coupling element additionally is provided with an annular sealing member which surrounds the penetrator and sealingly engages the interior of the connector. Keys on the annular sealing member and on the penetrator are provided to stop the annular sealing member against movement along the penetrator element in one position, and to allow movement in another position. This holds the annular sealing member against movement while pressure is applied during the removal of the protective member or pull tab. The connectors are maintained in alignment by the aligning shroud which constitues more than a major area of the opening of the connector.

Looking first at FIGS. 1 and 2 of the drawings, an enlarged tubular connector 12 is shown in cylindrical form. Another tubular connector 14 is also shown in cylindrical form and is of reduced diameter relative to tubular connector 12. Tubular connector 14 is provided with a closed end wall 15 to which a conduit coupler 16 is mounted. The conduit mounted to such coupler is joined to a blood component preparation or source.

The tubular connector 14 is in the form of a cylindrical housing in which is shown a tubular male coupling element 18 which has a passageway that is continuous with the conduit coupler 16. The opposite end of the tubular connector 14 has an open end defined by a thickened wall portion 20 with abutting continuous edge 20a and terminating shoulder 20b. A pressure cap 21 has a central passageway 21a in the end wall through which the cylindrical housing of connector 14 passes. Opposite camming pins 21b are fixed on the inside of the sidewall of cap 21 for coaction with cooperative means on the cylindrical housing of the other connector, to form an interlock at an overlapped junction, as will be seen.

The tubular connector 12 is also provided with a closed end wall 22 to which is mounted conduit coupler 23, similarly adapted to be joined to a conduit which is connected to a blood component preparation or source. The cylindrical housing of the tubular connector 12 is shown as containing a stationary and recessed tubular female coupling element 24 which opens inside a stationary penetrator element 25 having a penetrating end 26 formed in part by bevel 28 of the penetrator element. The penetrating end has a tapered edge which gradually widens to a ramming trailing edge 30. The recessed coupling element is adapted to directly engage the male coupling element 18 without contacting parts which can in any possible way communicate with the contaminating environment.

The stationary female coupling element 24 is shown with integrally formed keys 32 which are shown as extending along a substantial length of the coupling. The illustrated embodiment shows three support rods or keys 32 spaced by equal degrees along the outside of the tubular female coupling element. Such even spacing provides a three point support when pressure is applied to the joined connectors.

The connector 12 further houses an annular sealing member 34 which has a continuous side wall 35 and end wall 36. The end wall has a stop 37 which intercepts one of the keys 32 on the coupling element during rotation clockwise or anticlockwise for reasons which shall be made clear.

The annular sealing member 34 is provided with a central bore 38 through which the penetrator travels at a time when coupling engagement is made. The circular edge of the bore is notched with key seats 42 spaced apart 120°, as are the keys 32 on the coupler.

Reference to FIG. 5 will particularly help to further understand the following description. The annular sealing member 34 is rotated fully in one direction until one of the support rods or keys 32 intercepts the stop 37 on the end wall of the sealing member. In such a position, the keys are out of registration with the key seats 42 so that the annular sealing member 34 cannot be displaced when pressure is applied to the two abutted connector components. The keys 32, therefore, operate as support rods at such a time. Rotation of the annular sealing member in the opposite direction continues until a key 32 intercepts stop 37 and, in this second position, the keys on the coupling element and in the bore of the annular sealing member are in registration. The collective term "keys" relates to the support rods 32 on the coupling element and the key seats 42 in the annular sealing member.

Referring again particularly to FIGS. 1 and 2, it is seen that connector 12 has a modified open end defined by a trailing inner edge 44 and the leading outer edge 46. The trailing edge defines a minor portion of the opening area and the leading edge defines a major portion or a radius generated to more than 180°. The leading edge 46 terminates in a pair of truncating edges which define an opening or slot 47 therebetween. An undercut or slit 48 extends along the trailing edge 44, but such trailing edge encompasses a minor portion of the opening area, or is formed less than 180° along the radius. The leading and trailing edges are complementary edges drawn on a radius and are overlapping. The plane of the slit is normal to the axis of the slot, and such slot permits entry of a pull tab handle mounted to the other connector, whereby the handles may be aligned at the slot.

The slit 48 defines the rearward limits of a sleeve or shroud portion 50 which extends forwardly of the trailing edge 44 and the face of the annular sealing member which, in starting position, generally adjoins the trailing edge 44. The shroud or split sleeve receives the reduced diameter tubular connector 14 in the vestibule chamber 51. This assures positive alignment of the connectors as the major circumferential portion of the shroud locks the tube connectors against coaxial displacement.

A pair of camming grooves 52 are formed in the outside wall of the shroud, each having a dead end 52a and an opposite open end 52b. The dead end of one groove curves downwardly towards slot 47 while the dead end of the other groove curves upwardly away from the slot 47. The camming pins 21b coact with the camming grooves so the pressure cap 21 may urge connector 14 against annular seal 34 with a predetermined pressure load when the pins bottom against the dead ends of the locking grooves to provide a twist lock relationship. The illustrated interlock may also have the grooves on the inside of the pressure cap wall, and the pins on the outside of the shroud. In any event, the continuous wall of the pressure cap overlaps wall portions of the other connector, shown here as the shroud; and the interlock is formed at the overlapped junction.

Attention is now directed particularly to FIGS. 1, 3 and 4. An annular elastomeric gasket 53 is bonded to the face of the annular sealing member, and this gasket has the same general radial dimension as the annular face of the sealing member. A penetratable barrier assembly is mounted to the gasket 53, said assembly including a penetratable barrier 56 and a pull tab protective member 57. The pull tab protective member 57 includes a barrier cover 58 which is of the same general configuration as the barrier 56. The protective member further includes a fold or crease line 59 and a downwardly extending handle 60. The adhesive film, indicated schematically and portionally at 61, is substantially coextensive with the penetratable barrier 56 and the barrier cover 58.

In operation, the two connector components are positively aligned in abutting end to end relationship, and held in such alignment by the split sleeve or shroud portion 50. The support rods 32 hold the seal 34 as pressure cap 21 is locked. The handles 60 of the folded protective members are aligned and extend out of the slit 48. The pull tab on connector 12 orientates the seal 34 in supported position when the handle extends from the slit. The pull tabs are removed, as indicated schematically in FIG. 6, to progressively expose and adhere the sterile surfaces beneath the protective members. It is seen that the sterile and non-sterile surfaces are continuous on one side of the pull tab, and that the sterile surface is exposed and the protective barrier is invaginated in the sense that the sterile inner surface becomes the exposed outer surface. The aligned and adjoined pull tabs are removed through the slit 48 at the bottom of the shroud. The compressible gasket 53 may be gum rubber, and such provides a preliminary compressible seal which further facilitates closer contact of the barrier membranes for adhesive bonding. An elastomeric gasket may be associated with one or both of the barriers.

The penetratable barrier may be the plastic or metallic foils, such as aluminum. It has been found desirable to provide one of the barriers in the form of aluminum foil and the other barrier in the form of plastic film, such as fluorinated ethylene propylene (FEP, TEFLON), because such barriers have been found to be dielectrically attracted to each other when an adhesive film is present on each barrier. Further an aluminum foil barrier tends to reduce the distensibility of the plastic film barrier, while the plastic film barrier, in turn, tends to decrease the tendency of the aluminum foil barrier to tear upon penetraton when these materials are adhered to each other. The pull tabs are fabricated of readily flexible-thin materials which are easily invaginated, such as paper having sufficient strength to withstand the tension required for removal without tearing. Such paper contains on one surface a transferable adhesive film such that, when applied to the barrier, the adhesive film is separated from the tab and applied to the barrier membrane. The "differential adherence" is apparently due to the filler material and/or special treatment of the surfaces, such as by siliconizing. Several types of such preset film adhesives on paper are available, such as the Bostik Film No. 610-3, or Fasson Transfer Tape No. 140.

The surfaces of the tabs and barriers may be selected for differential adhesive qualities so that the adhesive remains either on a barrier membrane or is withdrawn with the pull tab resulting in application of the adhesive to one or both barrier membranes. The film of adhesive is necessarily present in at least one of the barrier assemblies. The protective barrier may be removably mounted in the other barrier assembly as by a continuous heat seal where the barrier and the protective member are both plastic. The protective barrier will still be removed by the pull tab technique of invagination as defined herein.

Figure 8:
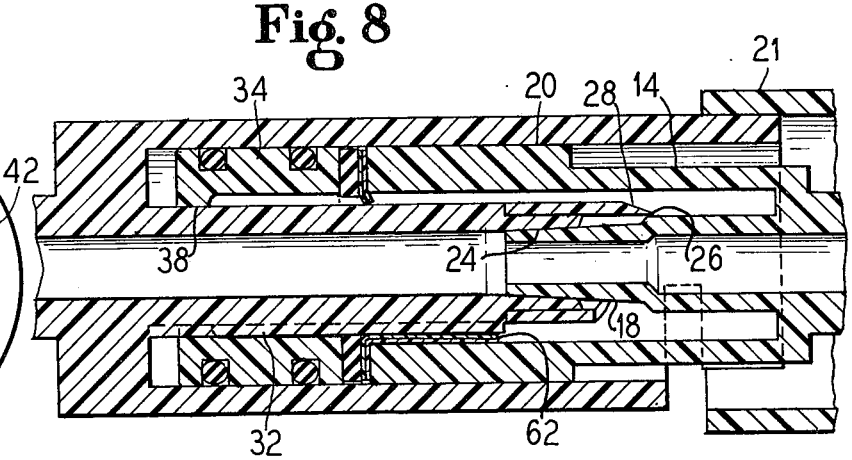
FIG. 8 is an elevational view in section, with portions removed, of the connector assembly previously illustrated, but showing the connected condition with the coupling elements engaged to provide a fluid path while excluding the environment.

After the pull tab is removed, and the barriers are adhered to each other, the annular sealing member is easily rotated by turning one of the connector components and holding the other stationary. Rotation of the annular sealing member aligns the keys into registration so that reduced diameter coupler 14 may be telescopically moved relative to tubular connector 12. This movement advances the annular sealing member towards the closed end 22 and moves the adhered barrier assemblies past the penetrating end of the stationary penetrator element housed within connector 12, and the penetrator moves though the area of adhesion on the barriers. The internal coupling elements are then engaged to provide the fluid path between the fluid sources, as shown in the view of FIG. 8. The flap 62 is pushed aside by the trailing ramming edge at the end of the penetrator element, and such flap does not interfere with the engagement of the coupling elements. The flap does not touch either internal couplers, nor do the couplers contact the margins of the opening formed during penetration. Thus, the fluid moves through said engaged coupling elements without contacting the penetrated barriers.

When used with blood component preparations, each connector will be sterilized together with its attached container used for supply or delivery of blood component preparations. The portions of each pull tab in contact with the barrier membranes and the barrier membranes and the adhesive are commonly sterile. Upon removal of the pull tabs, four actions occur:

1. the environmentally exposed outer portions of each pull tab, which comprises a contaminated area, are progressively replaced by an underlying sterile surface;
2. the sterile adhesive film is exposed on one or both barrier membranes;
3. the barrier membranes are drawn together and adhere to each other to exclude environmental contamination (applied pressure is no longer required after this occurrence);
4. the sealing member in one connector is bonded to the other connector so that said sealing member may be rotated to register the keys to effect relative movement between the adhesively joined barrier membrane and the penetrator element in one of the couplers.

Figure 9:
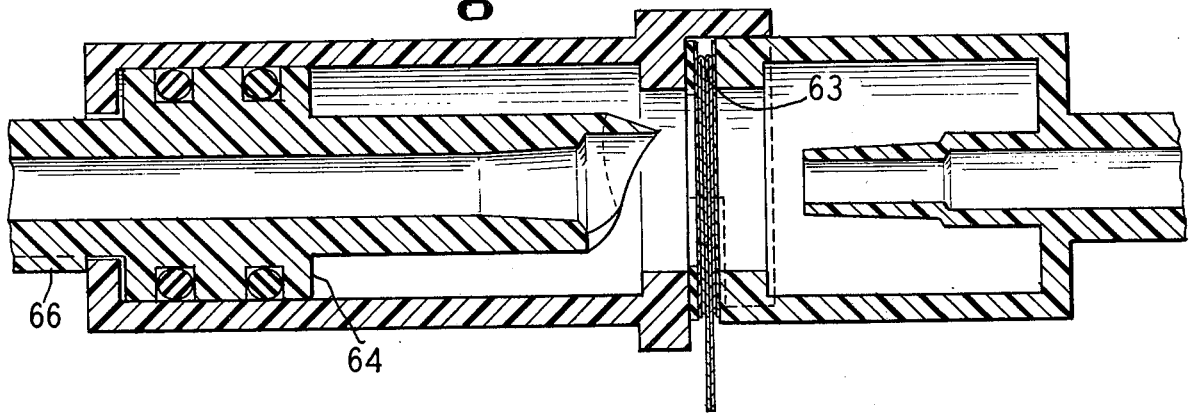
FIG. 9 is a side elevational view in section, with portions removed, of an alternative embodiment in which the connector components are abutted and a coupling element with a penetrating end is movable.
Figure 10:
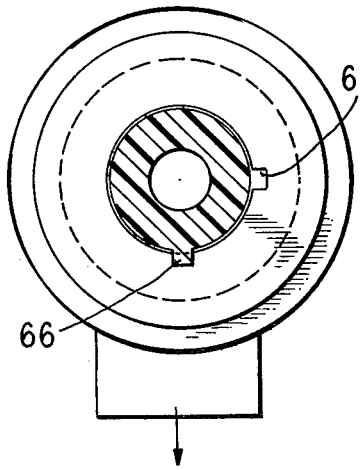
FIG. 10 is a sectional view taken along line 10—10 of FIG. 9.
Figure 11:
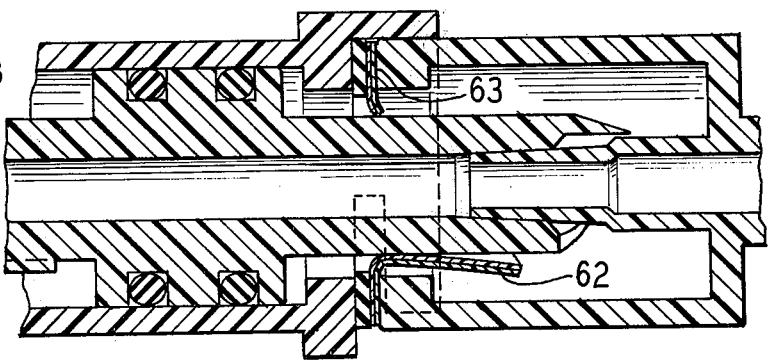
FIG. 11 is a side elevational view in section, with portions removed, similar to that of FIG. 9, but showing the connected condition with the coupling elements engaged to provide a fluid path while excluding the environment.

The alternative embodiment shown in FIGS. 9–11 is similarly constructed except that the coupler components are not telescopically engageable, but merely abut in end to end relationship. The penetrator element is not stationary but movable, and the connector with said penetrator element has a continuous flanged edge 63. The annular sealing member 64 is fixed to the penetrator element and may be integrally formed therewith. The penetrator element moves through openings 65 in the end of the connector coupling. A rib or key 66 is on the exterior of the penetrator element outside the connector, and said penetrator element is rotated exteriorly until such rib 66 is in registration with key seat or groove 68 in the end of the connector. The penetrator element may then be advanced to pierce the barrier assemblies so that the penetrator element enters the other connector and engages the male coupling element. As before, the penetrator may be in advance of a recessed coupling element.

The claims of the invention are now presented, and the terms of such claims may be better understood by referencd to the language of the foregoing specification.

What is claimed is:

1. A connector assembly for transferring fluids from one source to another under contaminant precluding conditions, including
   a first connector having one end for conduit connection to a fluid source and an opposite open end, a first tubular coupling element positioned within said first connector, said first tubular coupling element being communicable with said conduit connection, a penetrating end associated with said first tubular coupling element,
   a second connector having one end for conduit connection to a fluid source and an opposite open end, a second tubular coupling element positioned within said second connector, said second tubular coupling element being communicable with said conduit connection, said second tubular coupling element having an end engageable with said first tubular coupling element,
   a penetratable barrier assembly closing the open end of each of the connectors, each barrier assembly including a penetratable barrier and a removable protective member, an adhesive film covering a substantial portion of the area between the barrier and the protective member in at least one of said barrier assemblies, said protective member having a barrier portion covering the penetratable barrier, and a handle portion folded over the barrier portion and extending beyond the connector, said handle portions progressively exposing said adhesive film upon being pulled to progressively adhere the protective barriers to each other, and
   means to permit relative movement between the penetrating end and the adjoined barriers so that said penetrating end moves through said area of adhesion, said first coupling element engages said second coupling element to establish a fluid path after the adhered barriers are penetrated, said fluid moving through said engaged coupling elements without contacting the penetrated barriers on the penetrating end.

2. A connector assembly which includes the features of claim 1 wherein blood is transferred from one source to another under sterile conditions, wherein the penetratable barriers are bonded at the open end of each connector so that the interior of the connectors may remain sterile; and wherein each barrier assembly has an adhesive film between the barrier and the protective member.

3. A sterile connector assembly which includes the features of claim 2 wherein the connectors and coupling elements are cylindrical, and said first connector includes an annular sealing member surrounding the first tubular coupling element, said annular sealing member being sealingly movable relative to the interior surface of the first tubular connector.

4. A sterile connector assembly which includes the features of claim 3 wherein said annular sealing member is freely movable within the first connector and is aligned with the open end of the first connector, the penetratable barrier assembly being mounted only the annular sealing member and movable therewith, and said second connector being of reduced diameter relative to said first connector to allow telescopic engagement of the connectors and engagement of the coupling elements when the adjoined barrier assemblies and annular sealing member are moved past a stationary penetrating end associated with said first coupling element.

5. A sterile connector assembly which includes the features of claim 4, and which further includes an elastomeric annular gasket mounted at the open end of a connector, and said penetratable barrier being bonded, in turn, to said annular elastomeric gasket.

6. A sterile connector assembly which includes the features of claim 5, and which further includes a curved shroud at the open end of said first connector, and a leading edge defining a major portion of said opening and a slot defined by said minor portion, and a trailing edge adjoining the face of said freely movable annular sealing member, an undercut at said trailing edge defining a slit so that said leading and trailing edges are in overlapping relationship, whereby the handles of the protective members extend out of the slit when the connectors are adjoined, and are removable through said slit.

7. A sterile connector assembly which includes the features of claim 6, and which further include key elements on said first stationary coupling element, and key seats in said annular sealing member to receive said key elements when the annular sealing member is rotated to register the key seats and elements, and said key elements supporting the annular sealing member against applied pressure when positioned out of registry with the key seats.

8. A sterile connector assembly which includes the features of claim 7, and which further includes stop means on the back side of the annular sealing member to intercept the key elements on the coupling element in one rotated position so the key element and key seat are out of registry; and to intercept the keys in another rotated position so that the key element and key seat are in registry.

9. A sterile connector assembly which includes the features of claim 3 wherein said annular sealing member is fixed to the coupling element remote from the penetrating end, wherein the open ends of each connector has a flanged edge to facilitate edge to edge abuttment of the connectors, and wherein said first coupling element and fixed annular sealing member are movable to advance the penetrating end past the adjoined barrier assemblies and into said second connector so that the coupling elements may be engaged.

10. A sterile connector assembly which includes the features of claim 9, and which further includes a key element on said first coupling element located outside said first connector in preconnected condition, and a key seat in an end wall of said first connector, whereby rotation of the first coupling element correctly orients the piercing end relative to the adjoined barriers when the keys are in registration.

11. A sterile connector which includes the features of claim 10, and which further includes a curved shroud extending beyond the flanged end of one of the connectors, a major edge portion of the opening being defined by a leading edge on said shroud, and a minor portion of said opening comprising a slot extending to a trailing edge, an undercut slit at said trailing edge wherein said leading and trailing edges are in overlapping relationship.

12. A sterile connector assembly which includes the features of claim 3 wherein said penetrating end is a tubular member mounted to the first tubular coupling element in advance of the open end therof, whereby said first tubular coupling element is recessed in the penetrating end and directly engages the second coupling element in the other connector without contacting portions of the barrier assembly ruptured by the penetrator end.

13. A sterile connector assembly which includes the features of claim 3 and which further includes a thickened forward wall portion on one of the connectors, a shoulder between said thickened wall portion and the continuous housing wall of said one cylindrical connector, a pressure cap having a continuous side wall and an end wall, a central bore in the end wall, and the continuous wall of said one cylindrical connector passing through said central bore, said shoulder intercepted by said end wall, the continuous side wall of the pressure cap overlapping wall portions of the other cylindrical connector when the two connectors are adjoined at their open ends, and interlock means between the continuous wall of the pressure cap and the overlapped continuous wall portion, said interlock means positioned at said overlapped junction to force the end wall of the pressure cap against the continuous shoulder, thus supplying desired pressure to the adjoined barrier assemblies between the connectors.

14. A sterile connector assembly which includes the features of claim 13 wherein said annular sealing member is freely movable within the first connector and is aligned with the open end of the first connector, the penetratable barrier assembly being mounted only to the annular sealing member and movable therewith, and said second connector being of reduced diameter relative to said first connector to allow telescopic engagement of the connectors and engagement of the coupling elements when the adjoined barrier assemblies and annular sealing member are moved past a stationary penetrating end associated with said coupling element.

15. A sterile connector assembly which includes the features of claim 14 and which further includes an elastomeric annular gasket bonded to the face of the annular sealing member and said penetratable barrier being bonded, in turn, to said annular elastomeric gasket.

16. A sterile connector assembly which includes the features of claim 15 and which further includes a curved shroud at the open end of said first connector, and a leading edge defining a major portion of said opening, and a slot defined by said minor portion, and a trailing edge adjoining the face of said freely movable annular sealing member, an undercut at said trailing edge defining a slit so that said leading and trailing edges are in overlapping relationship, and said interlocking means being on the outside of said shroud and on the inside of said continuous wall of the pressure cap.

* * * * *